US009581536B2

(12) United States Patent
Ben-Yoav et al.

(10) Patent No.: US 9,581,536 B2
(45) Date of Patent: Feb. 28, 2017

(54) ANALYTICAL MICRO-DEVICES FOR MENTAL HEALTH TREATMENT MONITORING

(71) Applicant: University of Maryland, College Park, MD (US)

(72) Inventors: Hadar Ben-Yoav, Rockville, MD (US); Reza Ghodssi, Potomac, MD (US); Gregory F Payne, Hunt Valley, MD (US); Deanna L Kelly, York, PA (US); Eunkyoung Kim, Woodstock, MD (US); Thomas E Winkler, Greenbelt, MD (US)

(73) Assignees: UNIVERSITY OF MARYLAND, College Park, MD (US); UNIVERSITY OF MARYLAND, Baltimore, MD (US)

( * ) Notice: Subject to any disclaimer, the term of this patent is extended or adjusted under 35 U.S.C. 154(b) by 383 days.

(21) Appl. No.: 14/274,643

(22) Filed: May 9, 2014

(65) Prior Publication Data

US 2014/0332410 A1    Nov. 13, 2014

Related U.S. Application Data

(60) Provisional application No. 61/821,344, filed on May 9, 2013, provisional application No. 61/905,028, filed on Nov. 15, 2013.

(51) Int. Cl.
*G01N 27/327* (2006.01)
*G01N 15/10* (2006.01)
(Continued)

(52) U.S. Cl.
CPC .... *G01N 15/1056* (2013.01); *B01L 3/502707* (2013.01); *B01L 3/502715* (2013.01);
(Continued)

(58) Field of Classification Search
CPC .............. G01N 27/327; G01N 15/1056; B01L 2300/0363; B01L 2300/0645;
(Continued)

(56) References Cited

U.S. PATENT DOCUMENTS

| 2003/0213693 A1* | 11/2003 | Selvaganapathy | G01N 27/44791 |
| | | | 204/452 |
| 2008/0063566 A1* | 3/2008 | Matsumoto | G01N 33/5438 |
| | | | 422/68.1 |
| 2009/0142232 A1* | 6/2009 | Okada | B01L 3/502753 |
| | | | 422/72 |

OTHER PUBLICATIONS

Hong et al. (Biosensors and Bioelectronics 26 (2011) 3620-3626).*
(Continued)

*Primary Examiner* — Jennifer Dieterle
(74) *Attorney, Agent, or Firm* — Carter, DeLuca, Farrell & Schmidt, LLP

(57) ABSTRACT

A lab on a chip device includes a whole blood inlet port and microchannels to transport a whole blood sample or plasma skimmed from the whole blood sample into a detection chamber that includes at least one 3-electrode set of a counter electrode, a working electrode and a reference electrode. The counter electrode, the working electrode and the reference electrode may present bare, unmodified surfaces that are disposed so that clozapine present in the whole blood sample is detected via a reduction-oxidation reaction. Alternatively, the working electrode surface may include catechol grafted to chitosan. A method of detecting analytes and biomarkers includes collecting a whole blood sample, loading the sample into a point-of-care testing (POCT) device that includes at least one working electrode; testing the sample for the occurrence of a redox reaction; and calculating the total oxidative charge when the working electrode is bare or modified as before.

14 Claims, 9 Drawing Sheets

(51) Int. Cl.
  *B01L 3/00* (2006.01)
  *G01N 15/12* (2006.01)
  *G01N 15/00* (2006.01)

(52) U.S. Cl.
  CPC ... *B01L 3/502761* (2013.01); *B01L 3/502776* (2013.01); *G01N 15/1218* (2013.01); *G01N 27/3277* (2013.01); *B01L 2200/0636* (2013.01); *B01L 2200/0647* (2013.01); *B01L 2300/0636* (2013.01); *B01L 2300/0645* (2013.01); *B01L 2300/0816* (2013.01); *B01L 2300/0861* (2013.01); *B01L 2300/0887* (2013.01); *G01N 2015/008* (2013.01); *G01N 2015/1006* (2013.01); *G01N 2015/1062* (2013.01); *G01N 2015/1236* (2013.01); *G01N 2015/1254* (2013.01)

(58) Field of Classification Search
  CPC ..... B01L 2300/0816; B01L 2300/0861; B01L 2300/0887; B01L 2200/0647; B01L 2300/0636; B01L 3/502
  See application file for complete search history.

(56) References Cited

OTHER PUBLICATIONS

Wu, E.Q., et al., The Economic Burden of Schizophrenia in the United States in 2002. The Journal of Clinical Psychiatry, 2005. 66(9): p. 1122-1129.
Buchanan, R.W., et al., The 2009 Schizophrenia PORT Psychopharmacological Treatment Recommendations and Summary Statements. Schizophrenia Bulletin, 2010. 36(1): p. 71-93.
Conley, R.R., et al., Treatment-resistant Schizophrenic Patients Respond to Clozapine after Olanzapine Non-response. Biological Psychiatry, 1999. 46(1): p. 73-77.
Conley, R.R., et al., Comparison of clozapine use in Maryland and in Victoria, Australia. Psychiatr Serv, 2005. 56(3): p. 320-3.
Lieberman, J.A., Maximizing clozapine therapy: managing side effects. J Clin Psychiatry, 1998. 59 Suppl 3: p. 38-43.
Taylor, D.M., C. Young, and C. Paton, Prior antipsychotic prescribing in patients currently receiving clozapine: a case note review. J Clin Psychiatry, 2003. 64(1): p. 30-4.
Xiang, Y.T., et al., Clozapine use in schizophrenia: findings of the Research on Asia Psychotropic Prescription (REAP) studies from 2001 to 2009. Aust N Z J Psychiatry, 2011. 45(11): p. 968-75.
Kreyenbuhl, J., et al., Long-term combination antipsychotic treatment in VA patients with schizophrenia. Schizophr Res, 2006. 84(1): p. 90-9.
Mallinger, J.B., et al., Racial disparities in the use of second-generation antipsychotics for the treatment of schizophrenia. Psychiatr Serv, 2006. 57(1): p. 133-6.
Copeland, L.A., et al., Racial disparity in the use of atypical antipsychotic medications among veterans. Am J Psychiatry, 2003. 160(10): p. 1817-22.
Kelly, D.L., et al., Clozapine utilization and outcomes by race in a public mental health system: 1994-2000. J Clin Psychiatry, 2006. 67(9): p. 1404-11.
Weissman, E.M., Antipsychotic Prescribing Practices in the Veterans Healthcare Administration—New York Metropolitan Region. Schizophrenia Bulletin, 2002. 28(1): p. 31-42.
Agid, O., et al., Where to position clozapine: re-examining the evidence. Can J Psychiatry, 2010. 55(10): p. 677-84.
Kerwin, R., When should clozapine be initiated in schizophrenia?: Some arguments for and against earlier use of clozapine. CNS Drugs, 2007. 21(4): p. 267-78.
Hong, J. J.B. Edel, and A.J. deMello, Micro- and Nanofluidic Systems for High-throughput Biological Screening. Drug Discovery Today, 2009. 14: p. 134-146.
Yang, W. and A.T. Woolley, Integrated Multiprocess Microfluidic Systems for Automating Analysis. Journal of Laboratory Automation, 2010. 15: p. 198-209.
Craighead, H., Future Lab-on-a-Chip Technologies for Interrogating Individual Molecules. Nature, 2006. 442(7101): p. 387-393.
Dittrich, P.S. and A. Manz, Lab-on-a-Chip: Microfluidics in Drug Discovery. Nature Reviews Drug Discovery, 2006. 5 (3): p. 210-218.
Dutse, S.W. and N.A. Yusof, Microfluidics-Based Lab-on-Chip Systems in DNA-Based Biosensing: An Overview. Sensors, 2011. 11(6): p. 5754-5768.
Figeys, D. and D. Pinto, Lab-on-a-Chip: A Revolution in Biological and Medical Sciences. Analytical Chemistry, 2000. 72(9): p. 330 A-335 A.
Ghanim, M.H. and M.Z. Abdullah, Integrating Amperometric Detection with Electrophoresis Microchip Devices for Biochemical Assays: Recent Developments. Talanta, 2011. 85(1): p. 28-34.
Haeberle, S. and R. Zengerle, Microfluidic Platforms for Lab-on-a-Chip Applications. Lab on a Chip, 2007. 7(9): p. 1094-1110.
Jiang, H., X.A. Weng, and D.Q. Li, Microfluidic Whole-Blood Immunoassays. Microfluidics and Nanofluidics, 2011. 10 (5): p. 941-964.
Pollack, M.G., et al., Applications of Electrowetting-based Digital Microfluidics in Clinical Diagnostics. Expert Review of Molecular Diagnostics, 2011. 11(4): p. 393-407.
Trietsch, S.J., T. Hankemeier, and H.J. van der Linden, Lab-on-a-Chip Technologies for Massive Parallel Data Generation in the Life Sciences: A Review. Chemometrics and Intelligent Laboratory Systems, 2011. 108(1): p. 64-75.
Uhlen, M. and H.A. Svahn, Affinity Reagents for Lab on Chips. Lab on a Chip, 2011. 11(8): p. 1417-1419.
Mir, M., A. Horns, and J. Samitier, Integrated Electrochemical DNA Biosensors for Lab-on-a-Chip Devices. Electrophoresis, 2009. 30(19): p. 3386-3397.
Mark, D., et al., Microfluidic Lab-on-a-Chip Platforms: Requirements, Characteristics and Applications. Chemical Society Reviews, 2010. 39(3): p. 1153-1182.
Teles, F., L. Tavira, and L.J.P. da Fonseca, Biosensors as Rapid Diagnostic Tests for Tropical Diseases. Critical Reviews in Clinical Laboratory Sciences, 2010. 47(3): p. 139-169.
Rosen, Y. and P. Gurman, MEMS and Microfluidics for Diagnostics Devices. Current Pharmaceutical Biotechnology, 2010. 11(4): p. 366-375.
Lin, C.C., et al., Microfluidic Immunoassays. Jala, 2010. 15(3): p. 253-274.
Focke, M., et al., Lab-on-a-Foil: Microfluidics on Thin and Flexible Films. Lab on a Chip, 2010. 10(11): p. 1365-1386.
Varghese, S.S., et al., FRET for Lab-on-a-Chip Devices—Current Trends and Future Prospects. Lab on a Chip, 2010. 10(11): p. 1355-1364.
Liu, K.K., et al., Microfluidic Systems for Biosensing. Sensors, 2010. 10(7): p. 6623-6661.
Gupta, K., et al., Lab-on-a-Chip Devices as an Emerging Platform for Stem Cell Biology. Lab on a Chip, 2010. 10(16): p. 2019-2031.
Huo, D.Q., et al., Recent Advances on Optical Detection Methods and Techniques for Cell-Based Microfluidic Systems. Chinese Journal of Analytical Chemistry, 2010. 38(9): p. 1357-1365.
Wlodkowic, D. and J.M. Cooper, Tumors on Chips: Oncology Meets Microfluidics. Current Opinion in Chemical Biology, 2010. 14(5): p. 556-567.
Simon, E., Biological and Chemical Sensors for Cancer Diagnosis. Measurement Science and Technology, 2010. 21(11): p. 112002.
Didar, T.F. and M. Tabrizian, Adhesion based Detection, Sorting and Enrichment of Cells in Microfluidic Lab-on-Chip Devices. Lab on a Chip, 2010. 10(22): p. 3043-3053.
Koev, S.T., et al., Chitosan: An Integrative Biomaterial for Lab-on-a-Chip Devices. Lab on a Chip, 2010. 10(22): p. 3026-3042.
Lim, Y.C., A.Z. Kouzani, and W. Duan, Lab-on-a-Chip: A Component View. Microsystem Technologies-Micro-and Nanosystems-Information Storage and Processing Systems, 2010. 16(12): p. 1995-2015.

(56) References Cited

OTHER PUBLICATIONS

Hrncirik, P. and J. Nahlik, Novel Micro-scale Analytical Devices for On-line Bioprocess Monitoring: A Review. Chemical and Biochemical Engineering Quarterly, 2010. 24(4): p. 489-500.

Weddemann, A., et al., How to Design Magneto-based Total Analysis Systems for Biomedical Applications. Biosensors and Bioelectronics, 2010. 26(4): p. 1152-1163.

Webster, A., J. Greenman, and S.J. Haswell, Development of Microfluidic Devices for Biomedical and Clinical Application. Journal of Chemical Technology and Biotechnology, 2011. 86(1): p. 10-17.

Mohammed, M.I. and M.P.Y. Desmulliez, Lab-on-a-Chip Based Immunosensor Principles and Technologies for the Detection of Cardiac Biomarkers: A Review. Lab on a Chip, 2011. 11(4): p. 569-595.

Jang, A., et al., State-of-the-Art Lab Chip Sensors for Environmental Water Monitoring. Measurement Science and Technology, 2011. 22(3): p. 032001.

Sharma, H., et al., Unconventional Low-Cost Fabrication and Patterning Techniques for Point of Care Diagnostics. Annals of Biomedical Engineering, 2011. 39(4): p. 1313-1327.

Breier, A., et al., Effects of Clozapine on Positive and Negative Symptoms in Outpatients with Schizophrenia. The American Journal of Psychiatry, 1994. 151(1): p. 20-26.

Kane, J., et al., Clozapine for the Treatment-resistant Schizophrenic. A Double-blind Comparison with Chlorpromazine. Archives of General Psychiatry, 1988. 45(9): p. 789-796.

Azorin, J.M., et al., A Double-blind Comparative Study of Clozapine and Risperidone in the Management of Severe Chronic Schizophrenia. The American Journal of Psychiatry, 2001. 158(8): p. 1305-1313.

Volavka, J., et al., Clozapine, Olanzapine, Risperidone, and Haloperidol in the Treatment of Patients with Chronic Schizophrenia and Schizoaffective Disorder. The American Journal of Psychiatry, 2002. 159(2): p. 255-262.

Liu, Y., et al., Chitosan to Electroaddress Biological Components in Lab-on-a-Chip devices. Carbohydrate Polymers, 2011. 84(2): p. 704-708.

Gray, K.M., et al., Biomimetic Fabrication of Information-rich Phenolic-chitosan Films. Soft Matter, 2011. 7(20): p. 9601-9615.

Kim, E., et al., Amplified and In Situ Detection of Redox-Active Metabolite Using a Bio-based Redox-Capacitor. Analytical Chemistry, 2013. 85(4): p. 2102-2108.

Kim, E., et al., Reverse Engineering to Suggest Biologically-Relevant Redox Activities of Phenolic Materials. ACS Chemical Biology, 2013. In Press.

Kim, E., et al., Biomimetic Approach to Confer Redox Activity to Thin Chitosan Films. Advanced Functional Materials, 2010. 20(16): p. 2683-2694.

Payne, G.F., Y. Liu, and E. Kim. Novel Approach for Generating an Electrochemically Active Film with Amplification, Switching and Diode-like Behavior. In Isdrs '09. International Semiconductor Device Research Symposium, 2009. 2009.

Kauffmann, J.M., G.J. Patriarche, and G.D. Christian, Electrochemical Oxidation of Derivatives of Dibenzodiazepin. Dibenzothiazepin and Dibenzoxazepin. Analytical Letters, 1979. 12(11): p. 1217-1234.

Bard, A.J. and L.R. Faulkner, Electrochemical Methods: Fundamentals and Applications. 2nd ed. 2001, New York: John Wiley & Sons Inc.

Stark, A. and J. Scott, A Review of the Use of Clozapine Levels to Guide Treatment and Determine Cause of Death. Australian and New Zealand Journal of Psychiatry, 2012. 46(9): p. 816-825.

Couchman, L., et al., Plasma Clozapine, Norclozapine, and the Clozapine:Norclozapine Ratio in Relation to Prescribed Dose and Other Factors: Data From a Therapeutic Drug Monitoring Service, 1993-2007. Therapeutic Drug Monitoring, 2010. 32(4): p. 438-447.

Ben-Yoav, H., et al., A Microfluidic-based Electrochemical Biochip for Label-free Diffusion-restricted DNA Hybridization Analysis. Biosensors and Bioelectronics, 2012. 38(1): p. 114-120.

\* cited by examiner

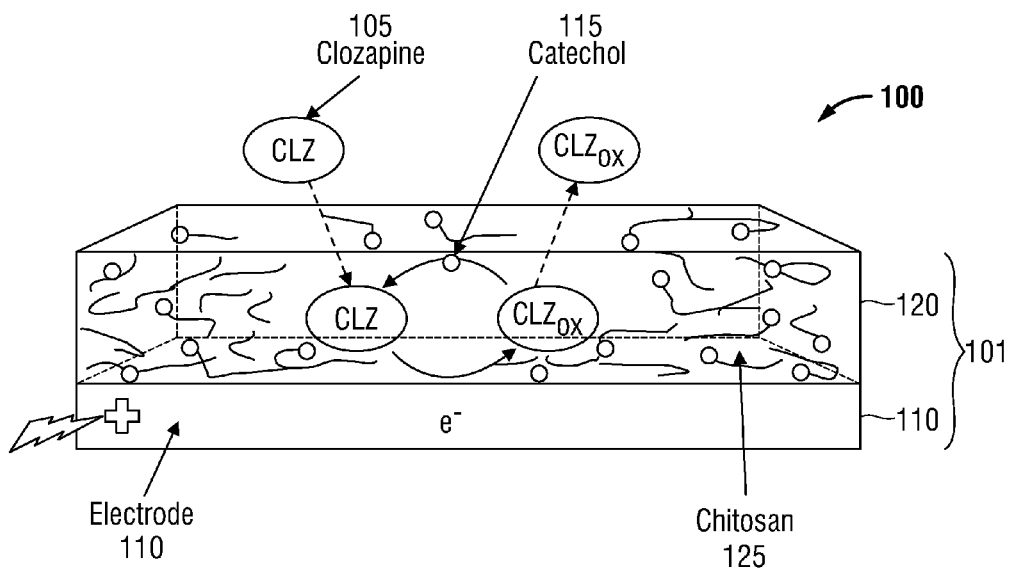
FIG. 1A
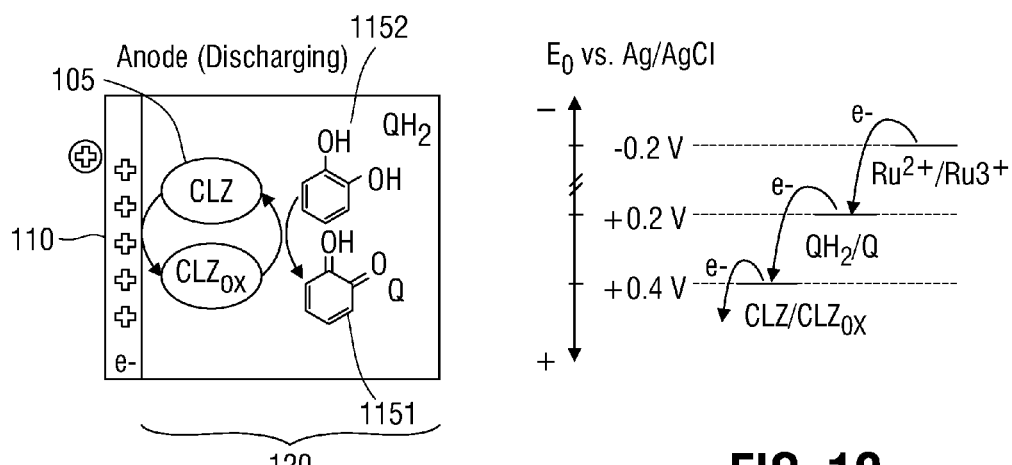
FIG. 1B
FIG. 1C

ANALYTICAL MICRO-DEVICES FOR MENTAL HEALTH TREATMENT MONITORING

CROSS-REFERENCE TO RELATED APPLICATIONS

This application claims the benefit of, and priority to, U.S. Provisional Patent Application No. 61/821,344, filed on May 9, 2013, entitled "Analytical Micro-Devices for Mental Health Treatment Monitoring" by Hadar Ben-Yoav et al., and U.S. Provisional Patent Application No. 61/905,028, filed on Nov. 15, 2013, entitled "System and Method for Monitoring Drug Treatment" by Hadar Ben-Yoav et al., the entire contents of both of which are incorporated by reference herein.

BACKGROUND

1. Technical Field

The present disclosure relates to the field of detection of substances present in biological fluids. More particularly, the present disclosure relates to devices, systems and methods for detection of clozapine and/or other substances in biological fluids such as blood.

2. Background of Related Art

One of the most disturbing problems facing the psychiatrist is when many inpatients and outpatients trusted to his or her care drop out of treatment before they have completed it to his or her satisfaction. This problem has usually been demonstrated in mental health disorders (19% of all mental health patients, 2002 figures) where chronic conditions require prolonged treatment with harsh and burdensome side effects. For example, schizophrenia is one of the most challenging and complex psychiatric disorders afflict humans. It is a lifelong and devastating illness that affects 1% of the population worldwide. The burden of the disorder is high with the estimated direct and indirect costs of the illness (2002 figures) to exceed $60 billion annually [1]. Currently there is no cure for the disorder and lifelong treatment with antipsychotics is recommended [2]. Approximately 30-50% of patients do not respond to first line psychiatric drug treatment. Clozapine (CLZ) is the only antipsychotic approved by FDA for treatment-resistant schizophrenia [3]. Despite the overwhelming evidence of the superior efficacy and effectiveness, CLZ is prescribed infrequently in the United States (less than 10% of all patients with schizophrenia), at a disproportionately lower rate than the estimated prevalence of treatment-resistant schizophrenia [4-6]. CLZ remains underutilized because of its frequent and invasive monitoring for plasma concentrations (weekly blood draws for white blood cells performed over the first six months), and adverse effects such as agranulocytosis, which is chief among them [5-12].

SUMMARY

The embodiments of the present disclosure provide a novel and non-obvious solution to the problems of mental health treatment as described above by providing a point of care testing (POCT) device that includes a whole blood inlet port in fluidic communication with microchannels extending therefrom. The microchannels are configured and disposed to transport a whole blood sample of a patient therethrough. The point-of-care testing device includes a detection chamber that includes at least one 3-electrode set of a counter electrode, a working electrode and a reference electrode wherein the counter electrode, the working electrode and the reference electrode present bare, unmodified surfaces that are disposed so that an analyte present in the whole blood sample is detected via an electrochemical reduction-oxidation reaction.

In one embodiment, at least the bare, unmodified surface of the working electrode of the at least one 3-electrode set includes catechol grafted to chitosan so that the analyte present in the sample is detected via an electrochemical reduction-oxidation reaction by the catechol-modified chitosan with the analyte.

In still another embodiment, at least the working electrode of the at least one 3-electrode set is formed of a nanotube material. The nanotube material may be selected from the group consisting of carbon; titanium nitride (TiN); or silicon/silicon dioxide/gold ($Si/SiO_2/Au$).

In yet another embodiment, the point of care testing device may further include a plasma skimming module that is configured and disposed to separate plasma from the whole blood sample prior to entry of the whole blood sample into the detection chamber.

In a still other embodiment, the analyte is clozapine.

The present disclosure relates also to a method of detecting analytes and biomarkers that includes collecting a whole blood sample of a subject, loading the sample into a point-of-care testing (POCT) device that includes at least one working electrode of at least one 3-electrode set; testing the sample for the occurrence of a redox reaction; calculating the total oxidative charge when at least the at least one working electrode of the at least one 3-electrode set presents a bare, unmodified surface to the sample.

In one embodiment, the method includes, wherein the bare, unmodified surface of the at least one working electrode is modified to include chitosan modified by catechol, testing the whole blood sample for the occurrence of a redox reaction at the surface that includes chitosan modified by catechol and calculating the total oxidative or reductive charge when at least the at least one working electrode of the at least one 3-electrode set presents to the sample the surface that includes chitosan modified by catechol.

In yet another embodiment, following the step of collecting the whole blood sample and prior to the step of loading the sample, the method includes skimming plasma from the whole blood sample and loading the plasma into the point of care testing device.

BRIEF DESCRIPTION OF THE DRAWINGS

These and other advantages will become more apparent from the following detailed description of the various embodiments of the present disclosure with reference to the drawings wherein:

FIG. 1A is s schematic diagram of a catechol-modified system with diffusing clozapine (CLZ) according to one embodiment of the present disclosure;

FIG. 1B is a schematic diagram of the catechol-modified system of FIG. 1A illustrating continuous oxidation of CLZ in the presence of catechol (Q) reduction;

FIG. 1C is a graphical plot of CLZ acting as an oxidizing mediator of Q, and $Ru^{2+}$ as the reducing mediator regenerating the Q wherein the vertical axis represents negative reduction potential $E_0$ in the upward direction and positive reduction potential $E_0$ in the downward direction versus Ag/AgCl;

DETAILED DESCRIPTION

Figure 2A:
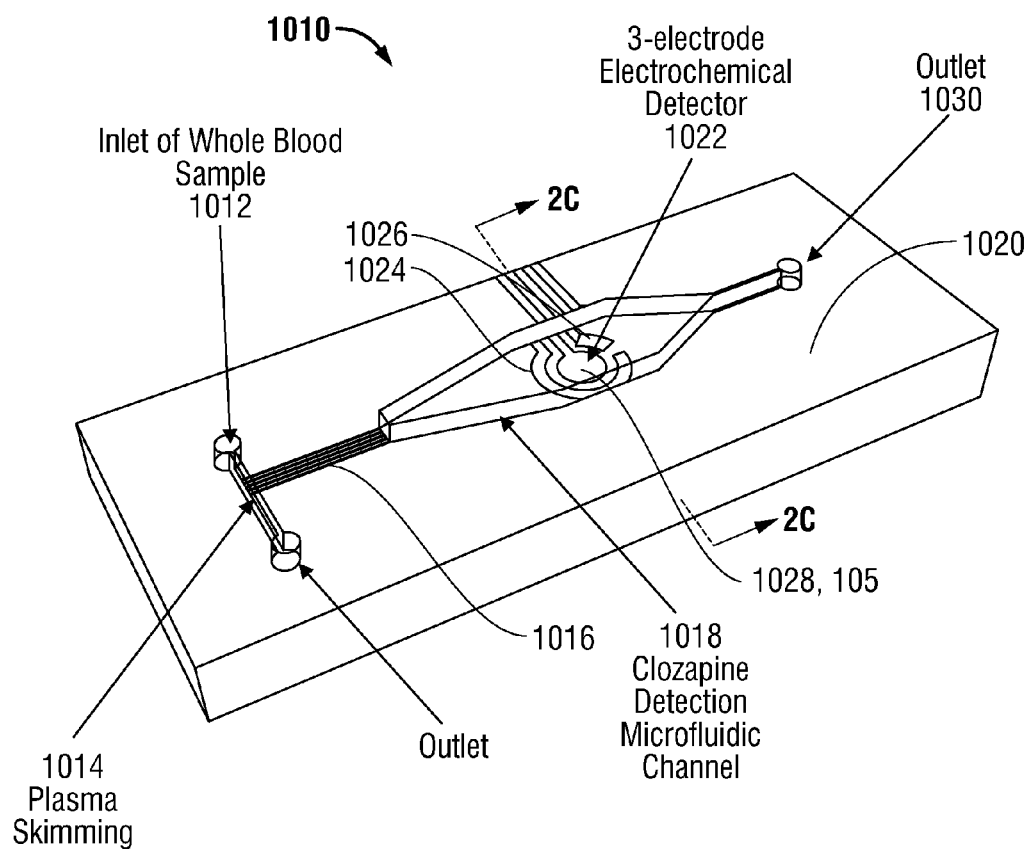
FIG. 2A illustrates a perspective view of an electrochemical lab-on-a-chip (LOC) device for clozapine detection that includes plasma skimming according to one embodiment of the present disclosure.

A biosensor that could provide prompt, real time monitoring of antipsychotic (e.g., CLZ) blood levels to determine if they are within an effective range but below levels associated with toxicity would be a significant advance in treatment [13, 14]. Further expansion towards identifying and monitoring side effects (e.g., white blood cells—WBC) and treatment efficacy biomarkers (e.g., metabolites) would simplify management of psychiatric drug treatment and encourage wider use of this medication for mental health patients who need it to achieve satisfactory symptom response. Currently there are no biosensors for objectively measuring blood levels of antipsychotics and safety biomarkers at the point of care (POC) in mental health. By real time monitoring of antipsychotic and safety biomarkers blood levels to maximize efficacy and minimize side effects, personalized treatment will improve overall mental health treatment success rates.

Microfluidic Lab-on-a-Chip (LOC) biosensing microsystems provide numerous advantages in clinical diagnostics, environmental monitoring, and biomedical research fields. These microsystems have the potential for functional integration with other technologies and miniaturization, leading to portability, high-throughput usage, and low-cost mass production. These translational technologies hold potential to improve upon the resolution, regulation, sensitivity, flexibility, and cost-savings over more traditional approaches, bringing bench top methods into the POC. Furthermore, LOC devices can provide a dense array of fluidic components and sensors at the micro-scale, which drastically reduce the necessary sample volumes, provide fast reaction rates, and can include integrated sensors [15-47]. By the application of microsystem devices to mental health analysis, various drug safety and efficacy biomarkers can be closely monitored. These devices will allow treatment teams to do blood analysis on-site in a fast, cost-effective, and straight forward method that will improve pre-clinical assessments and the overall chance of success of personalized medical care. Bringing biomaterials and microsystems technology into mental health discipline will lead to the development of novel portable LOC systems which can be utilized for real time antipsychotic treatment blood level detection, and efficacy and safety (toxicity) analysis of patients at the POC.

By addressing the urgent need for real time monitoring of blood antipsychotic levels, more rapid adjustment of dosage to reach a safe and effective blood level can be achieved. This approach could potentially reduce the cost and burden of monitoring, and increase the acceptability of psychiatric drug treatment to patients and prescribers. More important, it will lead to improved symptom control in treatment resistant patients and to reduced drop out. The incorporation of monitoring side effects and white blood cell counts make a LOC biosensing device attractive for POC use, decreasing costs and patient burden and changing the paradigm of how we currently monitor psychiatric drug treatment. This novel application of LOC monitoring of psychiatric drug treatment can revolutionize and provide a new model for mental health disorder research. It is a first step in personalized medical care that millions of mental health patients could benefit from worldwide.

Lab-on-a-Chip for Schizophrenia Treatment Monitoring

Schizophrenia is one of the most challenging and complex psychiatric disorders that afflicts humans. It is a lifelong and devastating illness and that affects 1% of the population worldwide. The burden of the disorder is high with the estimated direct and indirect costs of the illness (2002 figures) to exceed $60 billion annually [1]. Currently there is no cure for the disorder and lifelong treatment with antipsychotics is recommended [2]. CLZ is the most effective antipsychotic treatment for chronic and treatment refractory patients with schizophrenia. It is the only antipsychotic that has been FDA-approved for treatment-resistant schizophrenia and it provides effective treatment even when patients do not respond to other second-generation antipsychotics [3]. No existing first or second-generation antipsychotic is as effective as CLZ monotherapy in treatment-resistant patients [2, 48-51].

Despite the overwhelming evidence of the superior efficacy and effectiveness of CLZ compared to other antipsychotics in treatment-resistant schizophrenia, CLZ is prescribed infrequently in the United States, at a disproportionately lower rate than the estimated prevalence of treatment-resistant schizophrenia [4-6]. Although CLZ is available in generic formulations and is widely used in other countries (20-38% for schizophrenia patients [4, 7, 12]), the use of CLZ in the United States remains lower [4], (less than 10% of all patients with schizophrenia). Many thought leaders in schizophrenia believe that CLZ is grossly underutilized particularly because of the difficulty in monitoring for blood level concentrations to maximize efficacy (>350 ng/ml) and the frequent blood draws for side effects (WBC counts) [5-12]. Not only is it underutilized but blood levels are not drawn on all patients receiving CLZ despite standardized guidelines recommending this to be done in order to maximize efficacy [2]. In current practice, CLZ patients have many blood draws occurring to monitor WBC counts, but must also be scheduled for other blood draws to assay CLZ concentrations for dosage adjustments. This includes extra communication between physicians and patients, arranging times and transportation for extra visits to the office, coordinating and calling laboratories to get the results back immediately and the inconvenience of the patient to have to arrange this weekly. These blood draws, and the time lag in receiving reports on blood concentrations, add several more visits to the caregivers' treatment plan, which may not be feasible or practical for the patient or the treatment team. There is an urgent need for real time monitoring of blood CLZ levels. Real time monitoring could provide more rapid adjustment of dosage to reach a safe and effective blood level, potentially reduce the cost and burden of monitoring, and increase the acceptability of CLZ treatment to patients and prescribers, leading to improved symptom control in treatment resistant patients. The technological breakthrough could lead to much more extensive use of the underutilized medication CLZ. The improvement in care by creating a biosensor and decreasing blood drawn burden would be enormous [13, 14].

Microfluidic LOC biosensing microsystems provide numerous advantages in clinical diagnostics, environmental monitoring and biomedical research fields. These microsystems have the potential for functional integration with other technologies, leading to portability, high-throughput usage, and low-cost mass production. These translational technologies hold the potential to improve upon the resolution, regulation, sensitivity, flexibility, and cost-savings over more traditional approaches, bringing bench top methods into the POC. Furthermore, LOC devices can provide a dense array of fluidic components and sensors at the microscale which drastically reduce the necessary sample volumes, provide fast reaction rates, and can include integrated sensors [15-47]. By the application of microsystem devices to mental health analysis, various drug safety and efficacy biomarkers can be closely monitored. These devices will allow treatment teams to do blood analysis on-site in a relatively fast, cost-effective, and straightforward way that will improve pre-clinical assessments and the overall chance of success of personalized medical care. In this work, we develop a novel, low cost, high throughput, and portable biosensor based on microfluidic arrayed electrochemical LOC for controlled and rapid analysis of CLZ. As part of the device development, a novel biosensing mechanism is developed using an electrochemically responsive chitosan layer. The novel biosensor is utilized for real time with minimal pretreatment steps CLZ treatment serum level monitoring and efficacy and safety (toxicity) analysis of patients at the POC. The present disclosure relates to the integration of biomaterials and LOC technologies with CLZ treatment analysis, to achieve real time monitoring of the drug levels.

Thus, the present disclosure relates to an electrochemically-active biomaterial probe for schizophrenia treatment monitoring and integration of the biomaterial probe in LOC devices. More particularly, the present disclosure relates to in situ CLZ sensing based on an electrochemically-active biomaterial for CLZ oxidation amplification. The naturally derived polysaccharide chitosan, a very versatile biomaterial [40, 52], employed as a scaffold for subsequent modification with an electrochemically-active catechol, results in a redox cycling system [53-57].

FIG. 1A illustrates schematically a bioamplifier or electrochemical device 101 that executes a method of signal amplification for electrochemical detection of clozapine 105. The bioamplifier or electrical device 101 includes an overpotential electrode 110 and, in the example of FIG. 1A, a catechol-modified chitosan redox cycling system 120 in electrochemical communication with the overpotential electrode 110.

The redox cycling system 120 includes grafted catechol moieties 115 that can be inter-converted between oxidized (Q) forms 1151 and reduced ($QH_2$) forms 1152 ($E_0$=+0.2 V vs. Ag/AgCl). CLZ ($E_0$=+0.4 V vs. Ag/AgCl) that can diffuse freely within the chitosan film 125. Following oxidation of the CLZ 105 upon the electrode 110, the CLZ 105 is reduced by the grafted $QH_2$ moieties 1152, and under overpotential conditions, the CLZ 105 is electrochemically re-oxidized at the electrode 110 (see FIGS. 1A and 1C).

As defined herein, a bioamplifier refers to an electrochemical device that detects and amplifies an electrical signal, e.g., current or voltage or impedance or inductance, etc., emitted by a biological fluid such as blood or serum or plasma or urine or saliva or sweat or tears or cerebrospinal fluid etc., and is not limited to detecting and amplifying electrical signals emitted by anatomical features such as the heart or muscle, etc.

As defined herein, an overpotential electrode refers to the state of the electrode when the redox cycling reaction occurs as the electrode is not always in a positive potential in reference to other electrodes. The state of the electrode when this oxidation reaction occurs is when the electrode is in a potential that is relatively more positive than the standard reduction potential ($E_0$) of the reaction to be measured, or the state of the electrode when this reduction reaction occurs is when the electrode is in a potential that is relatively more negative than the standard reduction potential ($E_0$) of the reaction to be measured, e.g., the CLZ oxidation/reduction reaction.

FIG. 1B illustrates that a continuous cycle of reduction of CLZ 105 in the presence of catechol 115 followed by re-oxidation of CLZ 105 results from the application of CLZ 105 as an oxidizing mediator.

The continuous redox reaction increases the total charge transferred by CLZ oxidation, amplifying the generated electrochemical current and improving the signal-to-noise ratio. To recover the redox cycling system 120 to the reduced state, negative potential is applied in the presence of a reducing mediator, hexaammineruthenium (HARu, $Ru^{2+/3+}$, $E_0$=−0.2 V vs. Ag/AgCl).

Thus, the monitoring of clozapine may be performed by point of care providers who input a patient's blood sample to electrical device with or without the bioamplifier 101.

It is not necessary for the testing or monitoring of CLZ to be in the presence of HARu (or any reducing mediator). Other methodologies may be used such as by applying a negative potential (e.g. −0.4 V vs. Ag/AgCl) for a few minutes, e.g., generally about 2-3 minutes although time periods outside of this range may be determined to be effective also, on the catechol-chitosan system, i.e., the redox cycling system 120, in the presence of HARu (to reduce all the catechol molecules).

The "charging" solution is replaced with HARu in the CLZ detection chamber/channel (see FIG. 2A, microchannel 1018 described below) with the testing sample that has the CLZ. In the LOC setup it will mean that we flow one solution ("charging solution"), applying the negative potential for X time, then flowing the sample solution (where the "charging solution" flows out through the outlet), and applying the testing potential to sense CLZ in the sample.

The method includes applying a positive potential (with cyclic voltammetry (CV) or differential pulse voltammetry (DPV), Chronocoulometry, linear sweep voltammetry, step voltammetry or other related methods known in the art) on the modified electrode in the presence of CLZ (w/o HARu or any reducing mediator).

Both the benchtop scale and the LOC devices can be automated to do all of the above steps. A pumping system can be used to flow different solutions in the device in an automated way without the involvement of the user other than loading the sample. Alternatively, a user can load the necessary solutions and perform these steps by himself or herself if necessary.

Alternatively, when in the presence of bare, unmodified surface working electrodes, the clozapine may be detected by a redox reaction between the clozapine and the bare, unmodified surface, and not a redox cycling system.

Initially, the ability of the catechol-modified chitosan system to amplify the electrochemical current generated by CLZ was evaluated utilizing a gold electrode (7.5 mm×7.5 mm) in a test tube.

As to be described below in more detail, in one embodiment of the present disclosure, the CLZ is electrochemically sensed with a bare unmodified electrode (no chitosan, no catechol, no catechol-chitosan, without any film) with a whole blood sample (no pretreatment steps of adding any chemicals or doing any physical steps such as filtering, plasma skimming, etc. that are being used to remove some of the interfering molecules (such as proteins, cells, vitamins, other drugs, etc.) in the sample prior to testing.

In one embodiment, the bare, unmodified working electrode(s) may be formed of nano tubes or other materials such as platinum, carbon, etc.) and include different pretreatment steps (e.g. plasma skimming, filtering, chemicals to precipitate these interfering molecules, etc.) aspects. Examples of nanotubes include carbon, titanium nitride (TiN), or silicon/silicon dioxide/gold (Si/SiO2/Au). Examples are also described in U.S. patent application Ser. No. 14/190,060 filed Feb. 25, 2014, entitled "VIRAL NANOARRAYS AND SENSORS COMPRISING THE SAME", the entire contents of which are incorporated by reference herein.

Thus, from the perspective of a user of the bioamplifier or electrochemical device CLZ redox cycling system 120 for the detection of CLZ, in the simplest form, the method steps for detecting CLZ are simply to apply a whole blood sample to a chitosan coated electrode and to apply, at the benchtop scale, electrochemical analyzing equipment such as a potentiostat made by BioLogic, Inc. of Beijing, China, Princeton Applied Research, Oak Ridge, Tenn., U.S.A., or CH Instruments, Inc., Austin, Tex., U.S.A.

At the microscale, i.e., at a lab-on-a-chip scale for point of care applications, the method steps for detecting CLZ are also to apply a whole blood sample to a catechol-modified chitosan coated electrode. The electrochemical lab-on-a-chip (LOC) is patterned using microfabrication technology. Photolithography and wet etching processes are used to fabricate the LOC. 20 nm of chrome and 200 nm of gold were sputtered on 4 inch diameter silicon wafer insulated by 1000 nm of PECVD (plasma-enhanced chemical vapor deposition) silicon oxide. The chrome/gold coated wafers were patterned using photolithography to result in the gold electrodes features. Then a subsequential photolithography process resulted in insulating micrometer-thickness chambers defining a circular chamber with the 3-electrodes detector in the middle. The electrodes surface is cleaned with $O_2$ plasma clean to remove any organic residue. Then an on-chip Ag/AgCl reference electrode is fabricated by a subsequent 2-step electrodeposition method: 1) Ag electroplating, 2) AgCl generation. The wafer is diced into LOC chips where it is ready for the following biofabrication process of the catechol-chitosan redox system. An application of a 6 (not an obligation for this specific value) $A/m^2$ cathodic current density for 60 seconds is used to fabricate the chitosan film through an electrodeposition process (we can address the previous patent application by Ghodssi and Payne for chitosan electrodeposition process in micro-systems) as described in U.S. Patent Application Publication US 2007/0172821 A1 "ASSEMBLY OF CHITOSAN ONTO AN ELECTRODE SURFACE", by Wu et al., the entire contents of which are incorporated by reference herein. Then, the catechol is grafted on the chitosan films by immersion in 5 mM catechol and application of +0.6 V for 240 seconds, followed by immersion for 5 minutes in DI to discard unbound catechol.

The overall method to be performed would be measuring the current generated by a redox reaction, i.e. measuring the electrochemical current. That can be achieved by either potential sweep methods (cyclic voltammetry, differential pulse voltammetry, etc.) or potential step methods (chrono-amperometry, chrono-coulometry, etc.). Alternatively, electrochemical impedance may be employed.

For microscale LOC device applications, examples of portable electrochemical analyzing hardware with high throughput capabilities which may be utilized include (but also other vendors, or custom made electronics and packaging and equipment from vendors):

PalmSens—http://www.palmsens.com/en/ of Utrecht, The Netherlands:

Relevant equipment: MultiEmStat3 potentiostat that allows simultaneous measurement of 12 channels Ivium Technologies—http://www.ivium.nl/ of Eindhoven, The Netherlands:

Relevant equipment: PocketSTAT, CompactStat potentiostat connected with MultiWE32 module that allows simultaneous measurement of 32 channels.

BioLogic—http://www.bio-logic.info/ of Grenoble, France:

Relevant equipment: PG581 Portable Potentiostat/Galvanostat.

For macro-scale applications examples of electrochemical analyzing equipment (such as a potentiostat) which may be utilized include:

BioLogic—http://www.bio-logic.info/ of Grenoble, France

Princeton Applied Research http://www.princetonappliedresearch.com/index.aspx of Oak Ridge, Tenn., U.S.A.

CH Instruments—http://chinstruments.com/ of Austin, Tex., U.S.A.

Chitosan is electrodeposited by application of cathodic current. The local pH increase deprotonates the amine groups and insolubilizes the chitosan, resulting in a 700 nm thick film. Then, catechol is grafted by applying anodic current thereby bonding the oxidized form of the catechol to the chitosan amine group.

Since catechol is highly soluble in water, the catechol is oxidized by the application of a positive potential (+0.6 V vs. Ag/AgCl). This oxidation activates the catechol to chemically bond with the amine group of the chitosan.

To quantify and compare the ability of the system to amplify the signal generated by CLZ, an amplification factor (AF) is defined:

$$AF = \frac{(j_{w.CLZ} - j_{w/o\ CLZ})_{modified}}{(j_{w/CLZ} - j_{w/o\ CLZ})_{unmodified}}\bigg|_{@anodic\ peak} \quad (1)$$

Table 1 lists the AFs for four cases that have been studied. The catechol-modified chitosan film demonstrated the highest AF, more than 3 times that of either a bare electrode or catechol alone and 11-fold higher than chitosan-alone. The decreased electrochemical response of the chitosan-modified electrode likely results from the lower exposed surface area of the electrode due to the non-conductive chitosan coating. Furthermore, the porous structure of the chitosan may decrease the diffusion rate of CLZ towards the electrode, increasing the uncompensated resistance in the pores. Only the further functionalization of the chitosan matrix with the redox moiety catechol amplifies the charge transferred by CLZ oxidation, resulting in higher oxidation currents.

TABLE 1

Amplification factor (AF) calculated for the different modification steps of the catechol-chitosan system.

| Modification step | AF |
| --- | --- |
| Unmodified (bare) | 1.00 |
| Chitosan alone | 0.30 |
| Catechol alone | 1.05 |
| Catechol-modified chitosan | 3.33 |

These data and signal processing approaches could be also other methods of measuring other aspects of the electrochemical systems such as impedance, etc. which are not limited to current, voltage or charge or data processing such as background subtraction but may include other measurements such as signal-to-noise ratio or signal outputs from low and high pass filters, etc.

To characterize the biosensing performance of the redox amplifier, buffer solutions with known clozapine concentrations are used.

Figure 2B:
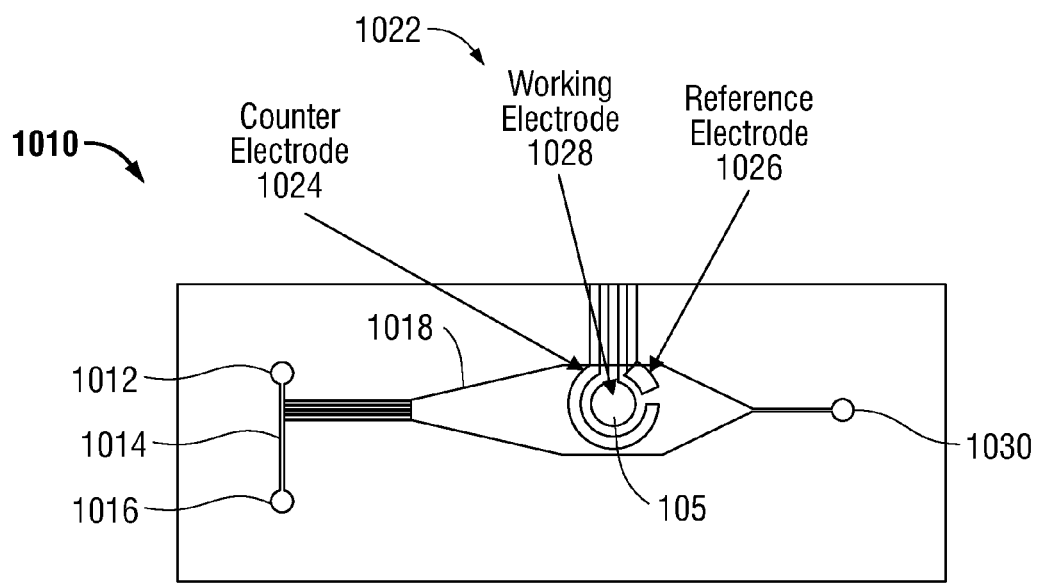
FIG. 2B is a view of a working surface the lab-on-a-chip device of FIG. 2A.
Figure 2C:
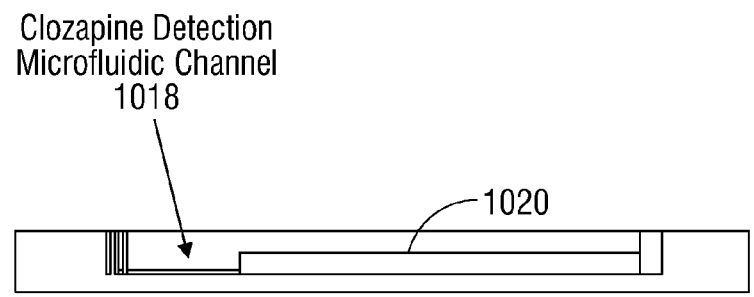
FIG. 2C is an elevation view of the lab-on-a-chip device of FIGS. 2A and 2B taken along section line 2C-2C of FIG. 2A.

FIGS. 2A, 2B and 2C illustrate an electrochemical lab-on-a-chip device 1010 that is functionally equivalent to the bioamplifier or electrical device 101 described above with respect to FIGS. 1A-1C. The electrochemical lab-on-a-chip (LOC) device 1010 for clozapine detection includes plasma skimming according to one embodiment of the present disclosure.

Referring to FIG. 2A, a whole blood sample is introduced at inlet port 1012 and runs through a plasma skimming module 1014, separating the blood cells from the plasma. The separated plasma 1016 flows into a clozapine detection microfluidic channel or recess or chamber 1018 (see also FIG. 2C) defined in upper or working surface 1020 where the CLZ 105 is electrochemically detected by a 3-electrode electrochemical detector 1022 (see also FIG. 2B). Thus, the plasma skimming module 1014 is configured and disposed to separate plasma 1016 from the whole blood sample prior to entry of the whole blood sample into the detection chamber 1018.

The 3-electrode electrochemical detector 1022 includes a linear strip having an arcuately shaped counter electrode tip 1024, a linear strip having an arcuately shaped reference electrode tip 1026 and a linear strip having a circularly shaped working electrode tip 1028 that is disposed in recess 1018 so that the counter electrode tip 1024 and the reference electrode tip 1026 are concentrically arranged around the working electrode tip 1028. The working electrode tip 1028 is modified with the redox cycling system 100 as described above with respect to FIGS. 1A-1C to amplify the electrochemical signal of clozapine CLZ 105 that is present in the blood sample 1016. Following signal detection by the electrochemical detector 1022 for the presence of CLZ 105, the separated plasma 1016 is then drawn out through the sample outlet port 1030 such as by application of a vacuum connection, not shown, or other means known in the art.

Figure 3A:
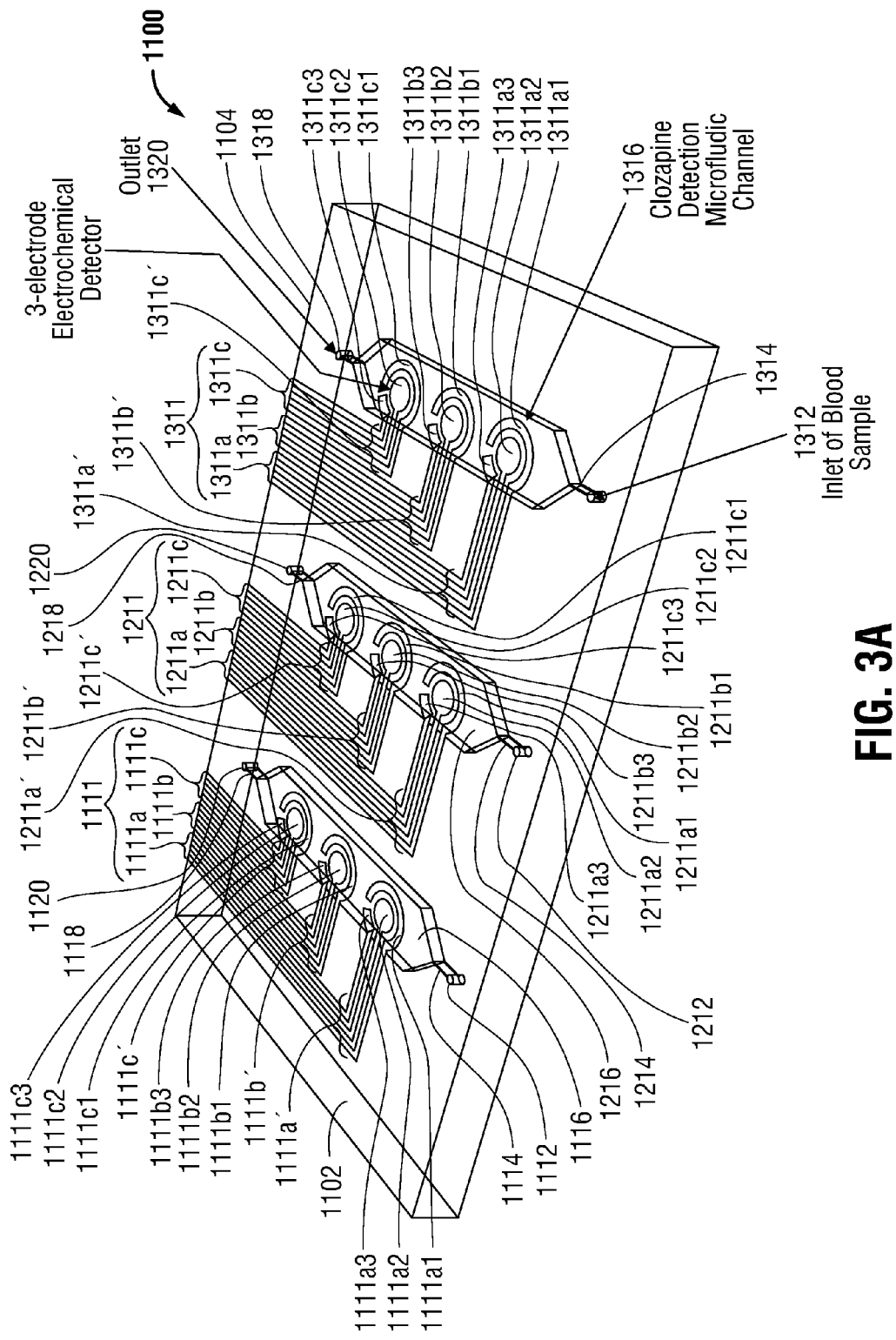
FIG. 3A illustrates a perspective view of an electrochemical lab-on-a-chip device for clozapine detection based on a whole blood sample according to one embodiment of the present disclosure.
Figure 3B:
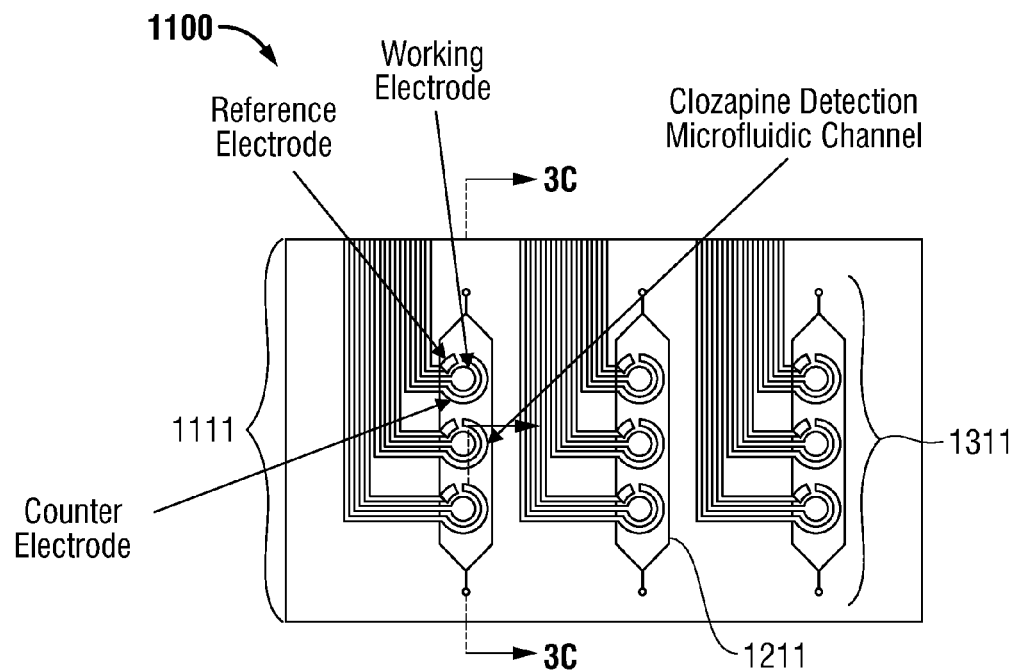
FIG. 3B is a view of a working surface the lab-on-a-chip device of FIG. 3A.
Figure 3C:
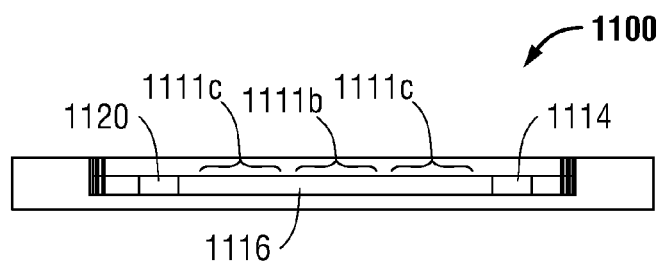
FIG. 3C is an elevation view of the lab-on-a-chip device of FIGS. 3A and 3B taken along section line 3C-3C of FIG. 3A.

FIGS. 3A-3C illustrate an electrochemical lab-on-a-chip device 1110 for clozapine detection based on a whole blood sample according to another embodiment of the present disclosure.

The electrochemical lab-on-a-chip device 1110 illustrated in FIGS. 3A, 3B and 3C is configured and disposed so that whole blood samples may be analyzed for clozapine, without plasma skimming. The electrochemical lab-on-a-chip device 1110 also includes multiple channels to enable concurrent measurements of multiple parameters. That is, the electrochemical lab-on-a-chip device 1110 enables repeatability of the CLZ detection test by preventing contamination and provides additional channels to test other types of solutions for control purposes (positive and negative controls). The additional channels may also be used to detect the presence of other types of analytes and biomarkers such as drugs, metabolites, vitamins, etc.

Referring to FIG. 3A, electrochemical lab-on-a-chip device 1100 includes a first multiple channel electrochemical detector group 1111, a second multiple channel electrochemical detector group 1211, and a third multiple channel electrochemical detector group 1311 each disposed generally in parallel to one another on an upper or working surface 1102 of the electrochemical lab-on-a-chip device 1100.

First multiple channel electrochemical detector group 1111 includes a whole blood sample inlet port 1112 at which a whole blood sample is introduced. The whole blood sample then flows through a microchannel 1114 into a first clozapine detection microfluidic detection channel or recess or chamber 1116 formed into the upper or working surface 1102. A first 3-electrode set 1111a is formed on the upper or working surface 1102 and extends orthogonally from an edge 1104 of the upper or working surface 1102 forming a right angle 1111a' and then runs parallel to the edge 1104 to drop in elevation with respect to upper or working surface 1102 to terminate in the first microfluidic detection channel or recess or chamber 1116. The first 3-electrode set 1111a includes a counter electrode 1111a1, a working electrode 1111a2 and a reference electrode 1111a3 that each follow the path described for the set 1111a to terminate in the in the first microfluidic detection channel or recess or chamber 1116.

Similarly, a second 3-electrode set 1111b is formed on the upper or working surface 1102 and extends orthogonally from edge 1104 of the upper or working surface 1102 forming a right angle 1111b' and then runs parallel to the edge 1104 to drop in elevation with respect to upper or working surface 1102 to terminate in the first microfluidic detection channel or recess or chamber 1116. The second 3-electrode set 1111b includes a counter electrode 1111b1, a working electrode 1111b2 and a reference electrode 1111b3 that each follow the path described for the set 1111b to terminate in the in the first microfluidic detection channel or recess or chamber 1116.

Additionally, a third 3-electrode set 1111c is formed on the upper or working surface 1102 and also extends orthogonally from edge 1104 of the upper or working surface 1102 forming a right angle 1111c' and then runs parallel to the edge 1104 to drop in elevation with respect to upper or working surface 1102 to terminate in the first microfluidic detection channel or recess or chamber 1116. The third 3-electrode set 1111c also includes a counter electrode 1111c1, a working electrode 1111c2 and a reference electrode 1111c3 that each also follow the path described for the set 1111c to terminate in the in the first microfluidic detection channel or recess or chamber 1116.

Upon completion of the sample testing in the first microfluidic detection channel or recess or chamber 1116, the tested blood sample then exits as waste through a microchannel 1118 and through an outlet port 1120 such as by application of a vacuum connection, not shown, or other means known in the art.

In a similar manner, second multiple channel electrochemical detector group 1211 includes a whole blood sample inlet port 1212 at which a whole blood sample is introduced. The whole blood sample then flows through a microchannel 1214 into a second clozapine detection microfluidic detection channel or recess or chamber 1216 formed into the upper or working surface 1102. A first 3-electrode set 1211a is formed on the upper or working surface 1102 and extends orthogonally from edge 1104 of the upper or working surface 1102 forming a right angle 1211a' and then runs parallel to the edge 1104 to drop in elevation with respect to upper or working surface 1102 to terminate in the second microfluidic detection channel or recess or chamber 1216. The first 3-electrode set 1211a includes a counter electrode 1211a1, a working electrode 1211a2 and a reference electrode 1211a3 that each follow the path described for the set 1211a to terminate in the second microfluidic detection channel or recess or chamber 1216.

Similarly, a second 3-electrode set 1211b is formed on the upper or working surface 1102 and also extends orthogonally from edge 1104 of the upper or working surface 1102 forming a right angle 1211b' and then runs parallel to the edge 1104 to drop in elevation with respect to upper or working surface 1102 to terminate in the second microfluidic detection channel or recess or chamber 1216. The second 3-electrode set 1211b includes a counter electrode 1211b1, a working electrode 1211b2 and a reference electrode 1211b3 that each follow the path described for the set 1211b to terminate in the in the second microfluidic detection channel or recess or chamber 1216.

As before, a third 3-electrode set 1211c is formed on the upper or working surface 1102 and also extends orthogonally from edge 1104 of the upper or working surface 1102 forming a right angle 1211c' and then also runs parallel to the edge 1104 to drop in elevation with respect to upper or working surface 1102 to terminate in the second microfluidic detection channel or recess or chamber 1216. The third 3-electrode set 1211c also includes a counter electrode 1211c1, a working electrode 1211c2 and a reference electrode 1211c3 that each also follow the path described for the set 1211c to terminate in the in the second microfluidic detection channel or recess or chamber 1216.

Again, upon completion of the sample testing in the second microfluidic detection channel or recess or chamber 1216, the tested blood sample then exits as waste through a microchannel 1218 and through an outlet port 20 such as by application of a vacuum connection, not shown, or other means known in the art.

In a still similar manner, third multiple channel electrochemical detector group 1311 includes a whole blood sample inlet port 1312 at which a whole blood sample is introduced. The whole blood sample then flows through a microchannel 1314 into a third clozapine detection microfluidic detection channel or recess or chamber 1316 formed into the upper or working surface 1102. A first 3-electrode set 1311a is formed on the upper or working surface 1102 and extends orthogonally from edge 1104 of the upper or working surface 1102 forming a right angle 1311a' and then runs parallel to the edge 1104 to drop in elevation with respect to upper or working surface 1102 to terminate in the third microfluidic detection channel or recess or chamber 1316. The first 3-electrode set 1311a includes a counter electrode 1311a1, a working electrode 1311a2 and a reference electrode 1311a3 that each follow the path described for the set 1311a to terminate in the third microfluidic detection channel or recess or chamber 1316.

Yet again, a second 3-electrode set 1311b is formed on the upper or working surface 1102 and also extends orthogonally from edge 1104 of the upper or working surface 1102 forming a right angle 1311b' and then runs parallel to the edge 1104 to drop in elevation with respect to upper or working surface 1102 to terminate in the third microfluidic detection channel or recess or chamber 1316. The second 3-electrode set 1311b includes a counter electrode 1311b1, a working electrode 1311b2 and a reference electrode 1311b3 that each follow the path described for the set 1311b to terminate in the third microfluidic detection channel or recess or chamber 1316.

Again as before, a third 3-electrode set 1311c is formed on the upper or working surface 1102 and also extends orthogonally from edge 1104 of the upper or working surface 1102 forming a right angle 1311c' and then also runs parallel to the edge 1104 to drop in elevation with respect to upper or working surface 1102 to terminate in the third microfluidic detection channel or recess or chamber 1316. The third 3-electrode set 1311c also includes a counter electrode 1311c1, a working electrode 1311c2 and a reference electrode 1311c3 that each also follow the path described for the set 1311c to terminate in the in the third microfluidic detection channel or recess or chamber 1316.

Again, upon completion of the sample testing in the third microfluidic detection channel or recess or chamber 1316, the tested blood sample then exits as waste through a microchannel 1218 and through an outlet port 20 such as by application of a vacuum connection, not shown, or other means known in the art.

When there are more than 4 groups of multiple channel electrochemical detector groups (electrochemical detectors), e.g., multiple channel electrochemical detector group 1111, 1211, 1311 and two additional groups, the repeatability of the measurement improves, which in turn improves the sensing performance. In addition, the electrochemical lab-on-a-chip device 1100 has parallel detection channels to perform positive (such as with a known concentration of CLZ; (e.g., via 3-electrode sets 1211a, 1211b, 1211c) and negative (only human plasma without CLZ; (e.g., via 3-electrode sets 1311a, 1311b, 1311c) control measurements. The nature of the working electrodes 1111a2, 1111b2, 1111c2 and 1211a2, 1211b2, 1211c2 and 1311a2, 1311b2, 1311c2 may be different from one another. For example, for the same channel, some of the electrochemical detectors will be modified with catechol-chitosan (e.g. 1311a2) and some only with chitosan (e.g. 1311b2). In this manner, differential measurement between both detectors analyzing the different intensities of the generated signals may be performed. Such a testing configuration and protocol allows the performance of one test of the electrochemical detector (either the catechol-chitosan or only the chitosan) with one sample as opposed to using only a catechol-chitosan electrochemical detector and performing two sequential electrochemical measurements with two different solutions. Such a testing configuration and protocol provides more accurate sensing performance when fouling of the electrochemical system occurs with human serum as the testing medium.

Figure 4A:
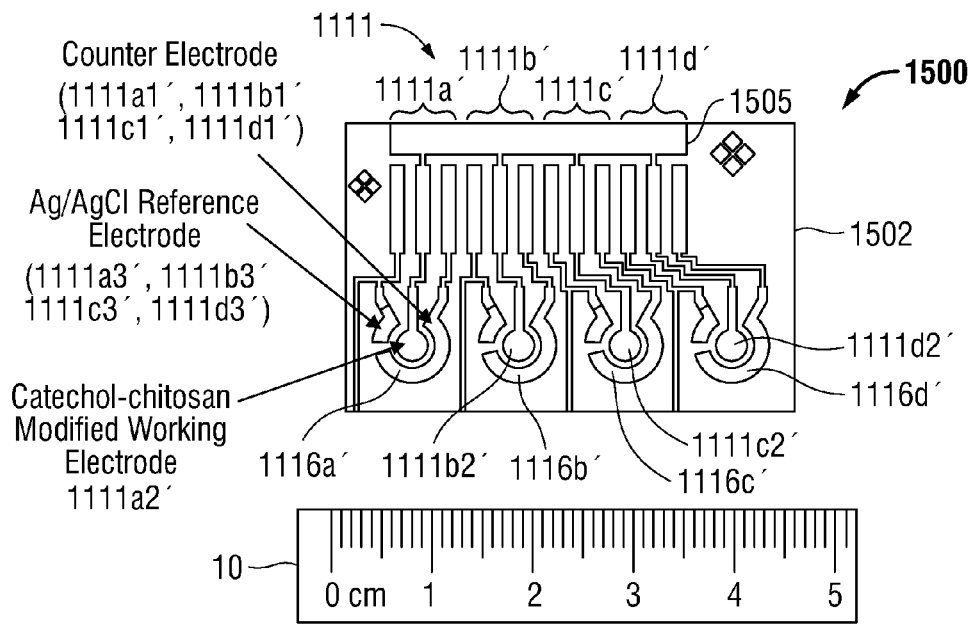
FIG. 4A is a photograph of an exemplary embodiment of an electrochemical LOC device partially fabricated according to the present disclosure.

FIG. 4A is a photograph of an exemplary embodiment of an LOC device 1500 fabricated according to the present disclosure shown in comparison to a 0-5 cm ruler 10. In the exemplary embodiment of FIG. 4A, the LOC device 1500 has a width dimension of approximately 3 cm and a length dimension of approximately 4.5 cm.

The LOC device 1500 includes at least four multiple channel electrochemical detector groups 1111$a'$, 1111$b'$, 1111$c'$ and 1111$d'$ that are substantially similar to the 3-electrode sets 1111$a$, 1111$b$, 1111$c$ of the multiple channel electrochemical detector group 1111 (or 1211 or 1311) described above. The four or more multiple channel electrochemical detector groups 1111$a'$, 1111$b'$, 1111$c'$ and 1111$d'$ are patterned on a Si/SiO$_2$ substrate 1502. A common bus bar may be provided to enable electrical communication between the 3 electrode sets 1111$a'$, 1111$b'$, 1111$c'$ and 1111$d'$.

The redox cycling system 120 (see FIGS. 1A-1C) was integrated onto working electrode tips 1111$a$2$'$, 1111$b$2$'$, 1111$c$2$'$ and 1111$d$2$'$ in the multi-chamber electrochemical LOC device 1500 by a bio-fabrication process that includes chitosan electrodeposition followed by catechol grafting. The LOC 1500 includes 4 chambers 1116$a'$, 11116$b'$, 1116$c'$, 1116$d'$, each with working (disk-shaped, 3 mm diameter) electrode tip 1111$a$2$'$, 1111$b$2$'$, 1111$c$2$'$, 1111$d$2$'$, counter electrode tips 1111$a$1$'$, 1111$b$1$'$, 1111$c$1$'$, 1111$d$1$'$ and reference electrode tips 1111$a$3$'$, 1111$b$3$'$, 1111$c$3$'$, 1111$d$3$'$, respectively. The aforementioned electrodes of LOC device 1500 were fabricated and patterned on the Si/SiO$_2$ substrate 1502 with a chrome/goldalloy material. The on-chip reference electrodes 1111$a$3$'$, 1111$b$3$'$, 1111$c$3$'$, 1111$d$3$'$ were fabricated of Ag/AgCl by a subsequent 2-step electrodeposition method.

A common bus bar 1505, made from a conductive material such as gold, is used for fabrication purposes when all the 4 working electrode tips 1111$a$2$'$, 1111$b$2$'$, 1111$c$2$'$, 1111$d$2$'$ in the respective chambers 1116$a'$, 1116$b'$, 1116$c'$, 1116$d'$ are simultaneously electrodeposited with chitosan. The simultaneous purpose is mainly to provide repeatability in the chitosan modification layer and to reduce the amount of time required for fabrication. The electrodeposition of the chitosan may be done also sequentially without the common bus bar 1505. There is no effect on the CLZ measurements when the measurements are performed sequentially without the common bus bar 1505 in place.

Figure 4B:
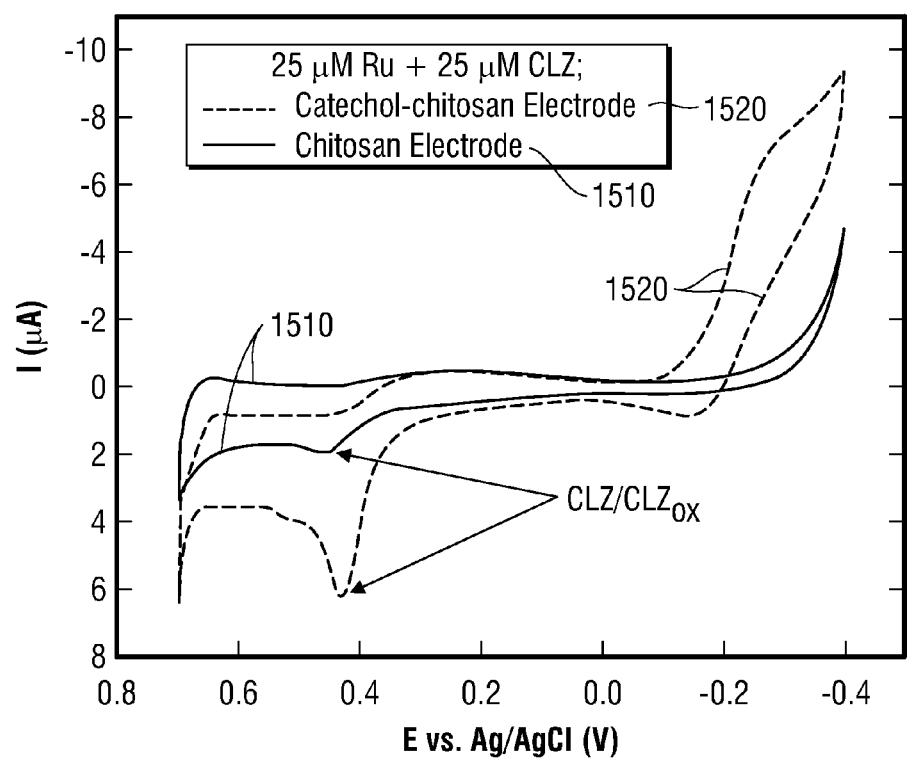
FIG. 4B is a graphical plot of CLZ sensed with either a catechol-chitosan modified electrode or a chitosan modified electrode wherein the vertical axis is current in microamps and the horizontal axis is applied potential in volts.

FIG. 4B illustrates the ability of the LOC device 1500 to amplify a clozapine signal. The oxidative current I (vertical axis measured in microamps) versus horizontal axis applied potential E in volts, generated by clozapine in the presence of the catechol-modified chitosan film 1520 is higher than chitosan modification 1510 alone.

There should be more than 4 groups of electrodes (electrochemical detectors) in the detection channel to improve repeatability of the measurement which will improve the sensing performance. In addition, the anticipated device would have parallel detection channels to perform positive (such as with a known concentration of CLZ) and negative (only human plasma without CLZ) control measurements.

For the same channel, some of the electrochemical detectors may be modified with catechol-chitosan and some only with chitosan. That way differential measurement between both detectors analyzing the different intensities of the generated signals may be performed. This allows performance of one test of the electrochemical detector (either the catechol-chitosan or only the chitosan) with one sample as opposed to using only a catechol-chitosan electrochemical detector and performing two sequential electrochemical measurements with two different solutions. The reason that it will provide better sensing performance is that fouling to the electrochemical system with human serum has been observed.

Figure 5:
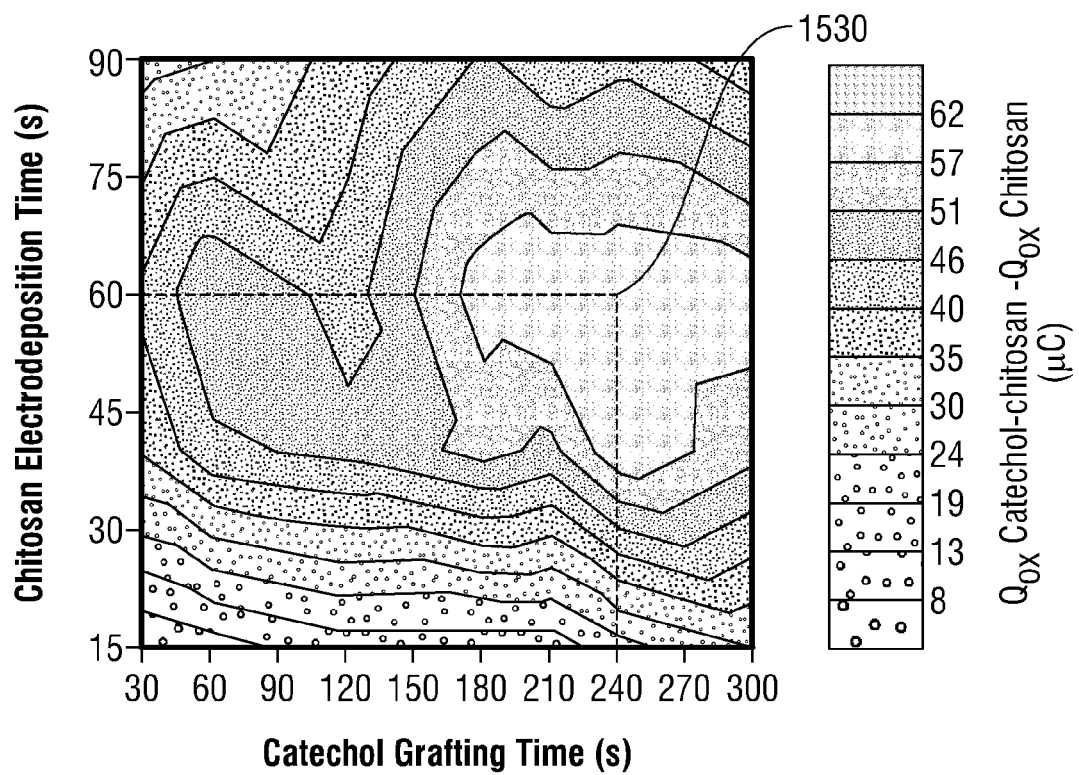
FIG. 5 is a graphical plot of chitosan electrodeposition time in seconds and the difference in oxidation current in microamps both plotted against catechol grafting time in seconds illustrating optimization of the chitosan thickness and the catechol grafting steps to maximize CLZ signal.

FIG. 5 illustrates the optimization of the chitosan thickness and the catechol density in the redox cycling system 120 on the LOC 1500. The chitosan thickness is positively related to the chitosan electrodeposition step duration time, as indicated by the left vertical axis measured in seconds. The catechol density is positively related to the catechol oxidation (grafting) step duration time, as indicated by the horizontal axis measured in seconds. The CLZ signal is quantified by calculating the total oxidative charge $Q_{ox\ catechol-chitosan}$ for the positive values of the applied potential (E>0 vs. Ag/AgCl) measured with catechol-modified chitosan electrode followed by subtracting the charge values $Q_{ox\ chitosan}$ calculated for chitosan alone, each measured in microcoulombs, as shown on the right vertical axis. The optimized values for maximizing CLZ signal are 60 seconds for the chitosan electrodeposition step and 240 seconds for the catechol grafting step, as represented by intersection point 1530.

Figure 6:
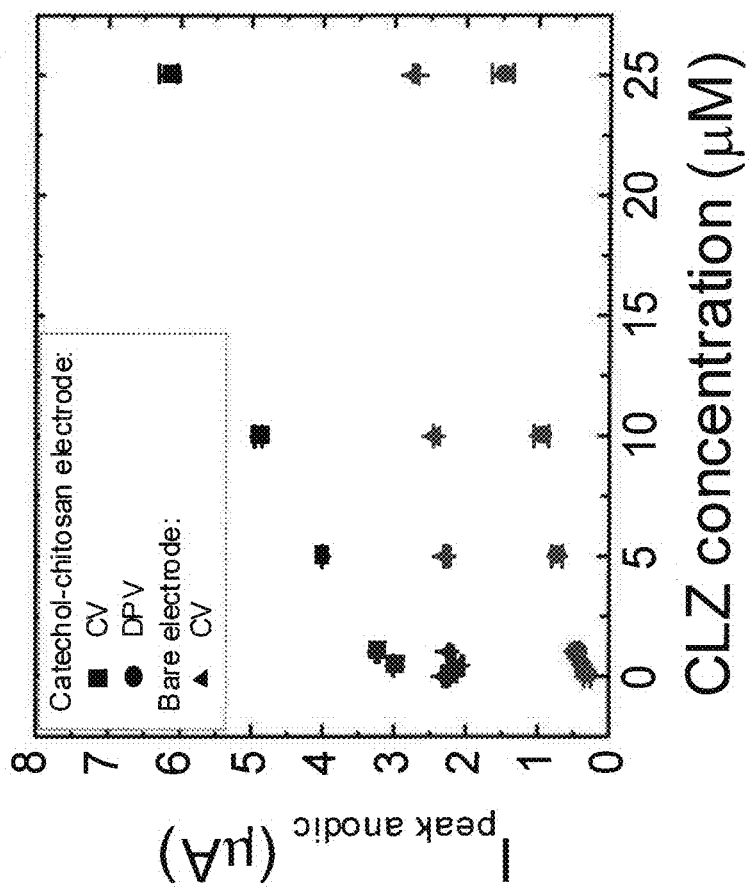
FIG. 6 is a graphical plot of CLZ dose response in buffer measured with the LOC wherein the CLZ dose response is measured in microamps on the vertical axis versus CLZ concentration in micromoles on the horizontal axis.

FIG. 6 illustrates CLZ dose response in buffer measured with the LOC device 1500. The figure presents the CLZ dose response measured with the LOC and the impact of the electrochemical measurement technique on the sensing performance. The oxidative current peak $I_{peak\ anodic}$, vertical axis measured in microcoulombs, generated by the clozapine is measured for 0.5, 1, 5, 10 and 25 μM CLZ concentration, horizontal axis, with either cyclic voltammetry (CV) or differential pulse voltammetry (DPV) with the catechol-modified chitosan electrode. The CV measurement technique yielded higher oxidative currents and better sensitivity than the DPV technique. For measurements at the microscale using the LOC device 1500, the buffer solution was phosphate buffer, 0.0027 M potassium chloride and 0.137 M sodium chloride, pH 7.4, at 25° C. For the macroscale data a 0.1 M phosphate buffer, pH 7, was utilized.

Figure 7:
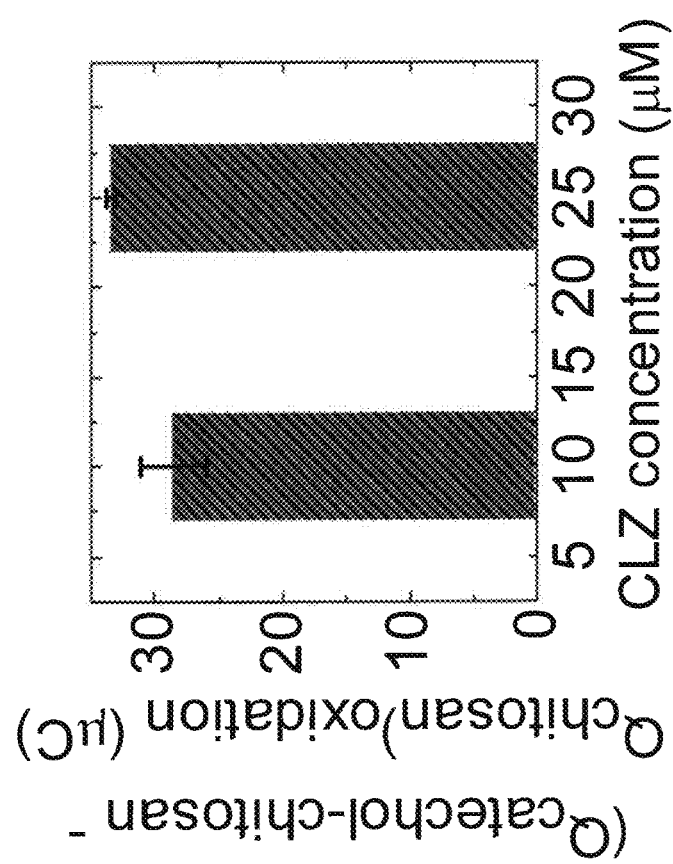
FIG. 7 is a graphical plot of CLZ detection in human serum with the LOC wherein the CLZ detection is measured in microcoulombs on the vertical axis versus CLZ concentration in micromoles on the horizontal axis.

FIG. 7 illustrates the ability of the LOC device 1500 to detect CLZ in human serum. Commercial human serum is spiked with either 10 uM or 25 uM CLZ, horizontal axis, and tested with the LOC device 1500. The CLZ signal is quantified by calculating the total oxidative charge Q for the positive values of the applied potential (E>0 vs. Ag/AgCl) measured with catechol-modified chitosan electrode followed by subtracting the charge values Q calculated for chitosan alone, vertical axis measured in microcoulombs. Results show that the LOC is able to differentiate between the 2 different CLZ concentrations.

A major challenge in the analysis of biological samples is the electrochemical reactivity and non-specific adsorption of molecules which cause fouling of the electrode. These molecules increase the background signal, decrease the signal-to-noise ratio, and deteriorate the sensitivity of the sensor. To validate that our approach is feasible in samples more complex than buffer solution, the sensing performance of the catechol-modified chitosan electrode system was characterized in human serum spiked with known CLZ concentrations. The high background signal attributed to other electro-active species decreased the signal-to-noise ratio and deteriorated the CLZ oxidation signal. Utilizing potential step technique would allow accumulating electrochemical reactions at specific potentials. While CLZ reoxidizes following catechol oxidation, other electro-active species, which are not being reduced by catechol, are consumed.

Chronocoulometry measurement of the transient charge at an overpotential value slightly higher than the standard reduction potential of CLZ will integrate the charge produced by CLZ re-oxidation over other electro-active species consumed by the electrochemical reaction, increasing the signal-to-noise ratio over time.

In view of the foregoing description of FIGS. 1A-7, it can be understood that the present disclosure relates to a method of detecting analytes and biomarkers, which in one exemplary embodiment includes clozapine. The method includes the following steps. Such as by a finger prick of a subject, the method includes obtaining and collecting a whole blood sample of a subject and loading the sample into a point-of-care testing (POCT) device, e.g., electrochemical LOC device 1010 with respect to FIGS. 2A-2C. The method may include skimming the sample and separating the sample into plasma and blood cells by plasma skimming module 1014. The method includes causing the plasma to flow into the CLZ detection channel or recess or chamber, e.g., chamber 1018. In one embodiment of the method, the whole blood sample is tested without skimming and separation into plasma 1016 and blood cells, e.g., using electrochemical LOC device 1110 with respect to FIGS. 3A-3C. In one channel 1116 of FIGS. 3A-3C, there are multiple sensors, e.g., multiple channel electrochemical detector group 1111 and respective 3-electrode sets 1111a, 1111b, 1111c, modified with either catechol-chitosan or chitosan alone. The method may include testing the sample simultaneously with the different sensors in the channel. There could be different options for the technique and the type of sensors In one embodiment, the method may also include calculating the total oxidative charge when at least the working electrode of at least one 3-electrode set presents a bare, unmodified surface to the sample, whether the sample is a whole blood sample or whether the sample has undergone plasma skimming by the plasma skimming module.

Referring to FIG. 5, the method includes calculating the total oxidative charge for potentials higher than 0 (E>0 vs. Ag/AgCl) for both the catechol-chitosan and the chitosan alone electrodes. The method includes calculating the oxidative charge for the chitosan alone electrode and subtracting the charge from the oxidative charge calculated for the catechol-chitosan electrode. The method may include comparing the subtracted oxidative charge value to a calibration curve that was previously prepared for different concentrations of CLZ (see FIGS. 6 and 7), in order to evaluate the accurate concentration of CLZ in the sample. In parallel to testing the sample in the CLZ detection channel, the method may include performing positive and negative controls in parallel channels. Performing positive control may be implemented by testing human serum with a known concentration of CLZ. Performing negative control may be implemented by testing human serum without CLZ.

In view of the foregoing, those skilled in the art will recognize that there may be different options for executing the technique and for the type of sensors utilized.

This work demonstrates the first utilization of a bio-amplifying LOC for clozapine sensing. Future work will focus on clinical monitoring of clozapine using samples from schizophrenia patients undergoing treatment. Next generation translational hybrid micro-devices that allow broader use of clozapine by decreasing costs and burden to the patient will personalize medical care and improve the lives of innumerable patients affected by this devastating illness.

Novel Features

The embodiments of the present disclosure present the following novel features.

Utilization of sensing microsystems for mental health disorders diagnostics and treatment.

Real-time, portable, continuous, low cost, and high throughput monitoring of mental health disorders drug treatment at the point-of-care and in-home use or in commercial laboratories, hospitals, pharmacies, physician's office.

In situ detection of biomarkers in blood serum

Differences from Present Technology

There is not current technology for real-time mental health treatment monitoring at the point-of-care. The current technology provides means to measure drugs and biomarkers in blood that are currently being analyzed in commercial laboratories. In these laboratories, specialized staff is analyzing the samples, and the process is costly and prolonged. Furthermore, the ability to have a continuous, real-time monitoring of drug treatment in mental health patients, will improve the chance of success of personalized medical care and will revolutionize the way mental health is being currently treated.

Although the present disclosure has been described in considerable detail with reference to certain preferred versions thereof, other versions are possible and contemplated. Therefore, the spirit and scope of the appended claims should not be limited to the description of the preferred versions contained therein.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope of the claims appended hereto.

REFERENCES

1. Wu, E. Q., et al., *The Economic Burden of Schizophrenia in the United States in* 2002. The Journal of Clinical Psychiatry, 2005. 66(9): p. 1122-1129.
2. Buchanan, R. W., et al., *The* 2009 *Schizophrenia PORT Psychopharmacological Treatment Recommendations and Summary Statements.* Schizophrenia Bulletin, 2010. 36(1): p. 71-93.
3. Conley, R. R., et al., *Treatment-resistant Schizophrenic Patients Respond to Clozapine after Olanzapine Nonresponse.* Biological Psychiatry, 1999. 46(1): p. 73-77.
4. Conley, R. R., et al., *Comparison of clozapine use in Maryland and in Victoria, Australia.* Psychiatr Serv, 2005. 56(3): p. 320-3.
5. Lieberman, J. A., *Maximizing clozapine therapy: managing side effects.* J Clin Psychiatry, 1998. 59 Suppl 3: p. 38-43.
6. Taylor, D. M., C. Young, and C. Paton, *Prior antipsychotic prescribing in patients currently receiving clozapine: a case note review.* J Clin Psychiatry, 2003. 64(1): p. 30-4.
7. Xiang, Y. T., et al., *Clozapine use in schizophrenia: findings of the Research on Asia Psychotropic Prescription (REAP) studies from* 2001 *to* 2009. Aust N Z J Psychiatry, 2011. 45(11): p. 968-75.

8. Kreyenbuhl, J., et al., *Long-term combination antipsychotic treatment in VA patients with schizophrenia.* Schizophr Res, 2006. 84(1): p. 90-9.
9. Mallinger, J. B., et al., *Racial disparities in the use of second-generation antipsychotics for the treatment of schizophrenia.* Psychiatr Serv, 2006. 57(1): p. 133-6.
10. Copeland, L. A., et al., *Racial disparity in the use of atypical antipsychotic medications among veterans.* Am J Psychiatry, 2003. 160(10): p. 1817-22.
11. Kelly, D. L., et al., *Clozapine utilization and outcomes by race in a public mental health system: 1994-2000.* J Clin Psychiatry, 2006. 67(9): p. 1404-11.
12. Weissman, E. M., *Antipsychotic Prescribing Practices in the Veterans Healthcare Administration—New York Metropolitan Region.* Schizophrenia Bulletin, 2002. 28(1): p. 31-42.
13. Agid, O., et al., *Where to position clozapine: re-examining the evidence.* Can J Psychiatry, 2010. 55(10): p. 677-84.
14. Kerwin, R., *When should clozapine be initiated in schizophrenia?: Some arguments for and against earlier use of clozapine.* CNS Drugs, 2007. 21(4): p. 267-78.
15. Hong, J., J. B. Edel, and A. J. deMello, *Micro-and Nanofluidic Systems for High-throughput Biological Screening.* Drug Discovery Today, 2009. 14: p. 134-146.
16. Yang, W. and A. T. Woolley, *Integrated Multiprocess Microfluidic Systems for Automating Analysis.* Journal of Laboratory Automation, 2010. 15: p. 198-209.
17. Craighead, H., *Future Lab-on-a-Chip Technologies for Interrogating Individual Molecules.* Nature, 2006. 442(7101): p. 387-393.
18. Dittrich, P. S. and A. Manz, *Lab-on-a-Chip: Microfluidics in Drug Discovery.* Nature Reviews Drug Discovery, 2006. 5(3): p. 210-218.
19. Dutse, S. W. and N. A. Yusof, *Microfluidics-Based Lab-on-Chip Systems in DNA-Based Biosensing: An Overview.* Sensors, 2011. 11(6): p. 5754-5768.
20. Figeys, D. and D. Pinto, *Lab-on-a-Chip: A Revolution in Biological and Medical Sciences.* Analytical Chemistry, 2000. 72(9): p. 330 A-335 A.
21. Ghanim, M. H. and M. Z. Abdullah, *Integrating Amperometric Detection with Electrophoresis Microchip Devices for Biochemical Assays: Recent Developments.* Talanta, 2011. 85(1): p. 28-34.
22. Haeberle, S. and R. Zengerle, *Microfluidic Platforms for Lab-on-a-Chip Applications.* Lab on a Chip, 2007. 7(9): p. 1094-1110.
23. Jiang, H., X. A. Weng, and D. Q. Li, *Microfluidic Whole-Blood Immunoassays.* Microfluidics and Nanofluidics, 2011. 10(5): p. 941-964.
24. Pollack, M. G., et al., *Applications of Electrowetting-based Digital Microfluidics in Clinical Diagnostics.* Expert Review of Molecular Diagnostics, 2011. 11(4): p. 393-407.
25. Trietsch, S. J., T. Hankemeier, and H. J. van der Linden, *Lab-on-a-Chip Technologies for Massive Parallel Data Generation in the Life Sciences: A Review.* Chemometrics and Intelligent Laboratory Systems, 2011. 108(1): p. 64-75.
26. Uhlen, M. and H. A. Svahn, *Affinity Reagents for Lab on Chips.* Lab on a Chip, 2011. 11(8): p. 1417-1419.
27. Mir, M., A. Homs, and J. Samitier, *Integrated Electrochemical DNA Biosensors for Lab-on-a-Chip Devices.* Electrophoresis, 2009. 30(19): p. 3386-3397.
28. Mark, D., et al., *Microfluidic Lab-on-a-Chip Platforms: Requirements, Characteristics and Applications.* Chemical Society Reviews, 2010. 39(3): p. 1153-1182.
29. Teles, F., L. Tavira, and L. J. P. da Fonseca, *Biosensors as Rapid Diagnostic Tests for Tropical Diseases.* Critical Reviews in Clinical Laboratory Sciences, 2010. 47(3): p. 139-169.
30. Rosen, Y. and P. Gurman, *MEMS and Microfluidics for Diagnostics Devices.* Current Pharmaceutical Biotechnology, 2010. 11(4): p. 366-375.
31. Lin, C. C., et al., *Microfluidic Immunoassays.* Jala, 2010. 15(3): p. 253-274.
32. Focke, M., et al., *Lab-on-a-Foil: Microfluidics on Thin and Flexible Films.* Lab on a Chip, 2010. 10(11): p. 1365-1386.
33. Varghese, S. S., et al., *FRET for Lab-on-a-Chip Devices—Current Trends and Future Prospects.* Lab on a Chip, 2010. 10(11): p. 1355-1364.
34. Liu, K. K., et al., *Microfluidic Systems for Biosensing.* Sensors, 2010. 10(7): p. 6623-6661.
35. Gupta, K., et al., *Lab-on-a-Chip Devices as an Emerging Platform for Stem Cell Biology.* Lab on a Chip, 2010. 10(16): p. 2019-2031.
36. Huo, D. Q., et al., *Recent Advances on Optical Detection Methods and Techniques for Cell-Based Microfluidic Systems.* Chinese Journal of Analytical Chemistry, 2010. 38(9): p. 1357-1365.
37. Wlodkowic, D. and J. M. Cooper, *Tumors on Chips: Oncology Meets Microfluidics.* Current Opinion in Chemical Biology, 2010. 14(5): p. 556-567.
38. Simon, E., *Biological and Chemical Sensors for Cancer Diagnosis.* Measurement Science and Technology, 2010. 21(11): p. 112002.
39. Didar, T. F. and M. Tabrizian, *Adhesion based Detection, Sorting and Enrichment of Cells in Microfluidic Lab-on-Chip Devices.* Lab on a Chip, 2010. 10(22): p. 3043-3053.
40. Koev, S. T., et al., *Chitosan: An Integrative Biomaterial for Lab-on-a-Chip Devices.* Lab on a Chip, 2010. 10(22): p. 3026-3042.
41. Lim, Y. C., A. Z. Kouzani, and W. Duan, *Lab-on-a-Chip: A Component View.* Microsystem Technologies-Micro- and Nanosystems-Information Storage and Processing Systems, 2010. 16(12): p. 1995-2015.
42. Hrncirik, P. and J. Nahlik, *Novel Micro-scale Analytical Devices for On-line Bioprocess Monitoring: A Review.* Chemical and Biochemical Engineering Quarterly, 2010. 24(4): p. 489-500.
43. Weddemann, A., et al., *How to Design Magneto-based Total Analysis Systems for Biomedical Applications.* Biosensors and Bioelectronics, 2010. 26(4): p. 1152-1163.
44. Webster, A., J. Greenman, and S. J. Haswell, *Development of Microfluidic Devices for Biomedical and Clinical Application.* Journal of Chemical Technology and Biotechnology, 2011. 86(1): p. 10-17.
45. Mohammed, M. I. and M. P. Y. Desmulliez, *Lab-on-a-Chip Based Immunosensor Principles and Technologies for the Detection of Cardiac Biomarkers: A Review.* Lab on a Chip, 2011. 11(4): p. 569-595.
46. Jang, A., et al., *State-Of-The-Art Lab Chip Sensors for Environmental Water Monitoring.* Measurement Science and Technology, 2011. 22(3): p. 032001.
47. Sharma, H., et al., *Unconventional Low-Cost Fabrication and Patterning Techniques for Point of Care Diagnostics.* Annals of Biomedical Engineering, 2011. 39(4): p. 1313-1327.
48. Breier, A., et al., *Effects of Clozapine on Positive and Negative Symptoms in Outpatients with Schizophrenia.* The American Journal of Psychiatry, 1994. 151(1): p. 20-26.

49. Kane, J., et al., *Clozapine for the Treatment-resistant Schizophrenic. A Double-blind Comparison with Chlorpromazine.* Archives of General Psychiatry, 1988. 45(9): p. 789-796.
50. Azorin, J. M., et al., *A Double-blind Comparative Study of Clozapine and Risperidone in the Management of Severe Chronic Schizophrenia.* The American Journal of Psychiatry, 2001. 158(8): p. 1305-1313.
51. Volavka, J., et al., *Clozapine, Olanzapine, Risperidone, and Haloperidol in the Treatment of Patients with Chronic Schizophrenia and Schizoaffective Disorder.* The American Journal of Psychiatry, 2002. 159(2): p. 255-262.
52. Liu, Y., et al., *Chitosan to Electroaddress Biological Components in Lab-on-a-Chip devices.* Carbohydrate Polymers, 2011. 84(2): p. 704-708.
53. Gray, K. M., et al., *Biomimetic Fabrication of Information-rich Phenolic-chitosan Films.* Soft Matter, 2011. 7(20): p. 9601-9615.
54. Kim, E., et al., *Amplified and In Situ Detection of Redox-Active Metabolite Using a Bio-based Redox-Capacitor.* Analytical Chemistry, 2013. 85(4): p. 2102-2108.
55. Kim, E., et al., *Reverse Engineering to Suggest Biologically-Relevant Redox Activities of Phenolic Materials.* ACS Chemical Biology, 2013. In Press.
56. Kim, E., et al., *Biomimetic Approach to Confer Redox Activity to Thin Chitosan Films.* Advanced Functional Materials, 2010. 20(16): p. 2683-2694.
57. Payne, G. F., Y. Liu, and E. Kim. *Novel Approach for Generating an Electrochemically Active Film with Amplification, Switching and Diode-like Behavior.* in ISDRS '09. International Semiconductor Device Research Symposium, 2009. 2009.
58. Kauffmann, J. M., G. J. Patriarche, and G. D. Christian, *Electrochemical Oxidation of Derivatives of Dibenzodiazepin. Dibenzothiazepin and Dibenzoxazepin.* Analytical Letters, 1979. 12(11): p. 1217-1234.
59. Bard, A. J. and L. R. Faulkner, *Electrochemical Methods: Fundamentals and Applications.* 2nd ed. 2001, New York: John Wiley & Sons Inc.
60. Stark, A. and J. Scott, *A Review of the Use of Clozapine Levels to Guide Treatment and Determine Cause of Death.* Australian and New Zealand Journal of Psychiatry, 2012. 46(9): p. 816-825.
61. Couchman, L., et al., *Plasma Clozapine, Norclozapine, and the Clozapine:Norclozapine Ratio in Relation to Prescribed Dose and Other Factors: Data From a Therapeutic Drug Monitoring Service, 1993-2007.* Therapeutic Drug Monitoring, 2010. 32(4): p. 438-447.
62. Ben-Yoav, H., et al., *A Microfluidic-based Electrochemical Biochip for Label free Diffusion-restricted DNA Hybridization Analysis.* Biosensors and Bioelectronics, 2012. 38(1): p. 114-120.

The invention claimed is:

1. A point of care testing (POCT) device comprising:
a whole blood inlet port in fluidic communication with microchannels extending therefrom, the microchannels configured and disposed to transport a whole blood sample of a patient therethrough; and
a detection chamber that includes at least one 3-electrode set of a counter electrode, a working electrode and a reference electrode wherein the counter electrode, wherein a surface of the working electrode comprises catechol grafted to chitosan and wherein a surface of the reference electrode is bare and unmodified and are disposed with respect to one another so that an analyte present in the whole blood sample is detected via an electrochemical reduction-oxidation reaction by the catechol-modified chitosan with the analyte.

2. The point of care testing device according to claim 1, wherein at least the working electrode of the at least one 3-electrode set is formed of a nanotube material.

3. The point of care testing device according to claim 1, wherein the nanotube material is selected from the group consisting of carbon; titanium nitride (TiN); or silicon/silicon dioxide/gold (Si/SiO$_2$/Au).

4. The point of care testing device according to claim 1, further comprising a plasma skimming module configured and disposed to separate plasma from the whole blood sample prior to entry of the whole blood sample into the detection chamber.

5. The point of care testing device according to claim 1, further comprising a plasma skimming module configured and disposed to separate plasma from the whole blood sample prior to entry of the whole blood sample into the detection chamber.

6. The point of care testing device according to claim 1, wherein the analyte is clozapine.

7. The point of care testing device according to claim 1, wherein the analyte is clozapine.

8. A method of detecting analytes and biomarkers, comprising:
collecting a whole blood sample of a subject,
loading the sample into a point-of-care testing (POCT) device that includes at least one working electrode of at least one 3-electrode set having a surface that is modified to include chitosan modified by catechol;
testing the whole blood sample for occurrence of a redox reaction at the surface that includes chitosan modified by catechol; and
calculating the total oxidative charge when at least the at least one working electrode of the at least one 3-electrode set includes at the surface chitosan modified by catechol.

9. The method according to claim 8, wherein following the step of collecting the whole blood sample and prior to the step of loading the sample, the method includes skimming plasma from the whole blood sample and loading the plasma into the point of care testing device.

10. The method according to claim 8, wherein following the step of collecting the whole blood sample and prior to the step of loading the sample, the method includes skimming plasma from the whole blood sample and loading the plasma into the point of care testing device.

11. The method according to claim 8, wherein the step of calculating includes calculating the one of the total oxidative or reductive charge, impedance, inductance or capacitance or combinations thereof under overpotential conditions.

12. The method according to claim 8, wherein the step of calculating includes calculating the one of the total oxidative or reductive charge, impedance, inductance or capacitance or combinations thereof under underpotential conditions.

13. The method according to claim 11, wherein the step of calculating the one of the total oxidative or reductive charge, impedance, inductance or capacitance or combinations thereof under overpotential conditions includes calculating one of electrical current or voltage under the overpotential conditions.

14. The method according to claim 12, wherein the step of calculating the one of the total oxidative or reductive charge, impedance, inductance or capacitance or combinations thereof under underpotential conditions includes calculating one of electrical current or voltage under the underpotential conditions.

\* \* \* \* \*